United States Patent [19]

Alcime et al.

[11] Patent Number: 5,632,772
[45] Date of Patent: May 27, 1997

[54] EXPANDABLE SUPPORTIVE BRANCHED ENDOLUMINAL GRAFTS

[75] Inventors: Rysler Alcime, Miami; Yasushi Kato, P. Pines; Leonard Pinchuk, Miami, all of Fla.

[73] Assignee: Corvita Corporation, Miami, Fla.

[21] Appl. No.: 558,028

[22] Filed: Nov. 13, 1995

Related U.S. Application Data

[63] Continuation-in-part of Ser. No. 140,245, Oct. 21, 1993, abandoned.

[51] Int. Cl.$^6$ ................................................... A61F 2/06
[52] U.S. Cl. ................................................ 623/1; 623/12
[58] Field of Search ................................. 623/1, 11, 12; 606/194, 195

[56] References Cited

U.S. PATENT DOCUMENTS

| | | | |
|---|---|---|---|
| 4,173,689 | 11/1979 | Lyman et al. | |
| 4,323,525 | 4/1982 | Bornat | |
| 4,459,252 | 7/1984 | MacGregor | |
| 4,475,972 | 10/1984 | Wong | |
| 4,512,338 | 4/1985 | Balko et al. | |
| 4,555,771 | 11/1985 | Wallsten | |
| 4,580,568 | 4/1986 | Gianturco | |
| 4,712,553 | 12/1987 | MacGregor | |
| 4,731,073 | 3/1988 | Robinson | 623/1 |
| 4,733,665 | 3/1988 | Palmaz | |
| 4,738,740 | 4/1988 | Pinchuk et al. | |
| 4,800,882 | 1/1989 | Gianturco | |
| 4,816,028 | 3/1989 | Kapadia et al. | 623/1 |
| 4,873,308 | 10/1989 | Coury et al. | |
| 4,878,908 | 11/1989 | Martin et al. | 623/1 |
| 4,950,227 | 8/1990 | Savin et al. | 604/8 |
| 4,954,126 | 9/1990 | Wallsten | 600/36 |
| 4,994,071 | 2/1991 | MacGregor | |
| 5,019,090 | 5/1991 | Pinchuk | 606/194 |
| 5,104,399 | 4/1992 | Lazarus | 623/1 |
| 5,116,360 | 5/1992 | Pinchuk et al. | 623/1 |
| 5,156,620 | 10/1992 | Pigott | 623/1 |
| 5,171,262 | 12/1992 | MacGregor | 623/1 |
| 5,195,984 | 3/1993 | Schatz | 606/195 |
| 5,236,447 | 8/1993 | Kubo et al. | 623/1 |
| 5,282,823 | 2/1994 | Schwartz et al. | 606/198 |
| 5,290,305 | 3/1994 | Inoue | 606/191 |
| 5,330,500 | 7/1994 | Song | 606/198 |
| 5,354,308 | 10/1994 | Simon et al. | 606/198 |
| 5,356,423 | 10/1994 | Tihon et al. | 606/194 |
| 5,360,443 | 11/1994 | Barone et al. | 606/191 |
| 5,385,580 | 1/1995 | Schmitt | 623/1 |
| 5,443,499 | 8/1995 | Schmitt | 623/1 |

FOREIGN PATENT DOCUMENTS

| | | | |
|---|---|---|---|
| 79302040 | 4/1980 | European Pat. Off. | |
| 91304988 | 12/1991 | European Pat. Off. | |
| 539237 | 4/1993 | European Pat. Off. | 623/1 |
| 3918736 | 12/1990 | Germany | |
| 1205743 | 9/1970 | United Kingdom | |
| 2115776 | 9/1983 | United Kingdom | |
| 2189150 | 10/1987 | United Kingdom | 623/1 |
| 9206734 | 4/1992 | WIPO | |
| 92009246 | 6/1992 | WIPO | 623/1 |
| 9401056 | 1/1994 | WIPO | |

*Primary Examiner*—Michael J. Milano
*Attorney, Agent, or Firm*—Lockwood, Alex, Fitzgibbon & Cummings

[57] ABSTRACT

An endoluminal graft which is both expandable and supportive is provided in a form suitable for use in a branched body vessel location. The graft expands between a first diameter and a second, larger diameter. The support component is an expandable stent endoprosthesis. A liner is applied to the endoprosthesis in the form of a compliant wall material that is porous and biocompatible in order to allow normal cellular invasion upon implantation, without stenosis, when the expandable and supportive graft is at its second diameter. The supportive endoluminal graft is preferably provided as a plurality of components that are deployed separately at the branching body vessel location, one of which has a longitudinal indent defining leg portions within which the other components fit in a telescoping manner.

36 Claims, 5 Drawing Sheets

EXPANDABLE SUPPORTIVE BRANCHED ENDOLUMINAL GRAFTS

CROSS REFERENCE TO RELATED APPLICATION

This is a continuation-in-part of application Ser. No. 140,245, filed Oct. 21, 1993, now abandoned.

BACKGROUND AND DESCRIPTION OF THE INVENTION

This invention generally relates to supportive endoluminal grafts which have the ability to be delivered transluminally and expanded in place to provide a graft that is endoluminally positioned and placed, with the aid of an appropriate inserter or catheter, and that remains so placed in order to both repair a vessel defect and provide lasting support at the location of the graft. In its broadest sense, the graft preferably combines into a single structure both an expandable luminal prosthesis tubular support component and a compliant graft component secured thereto. The expandable supportive endoluminal graft takes on a bifurcated or branched structure made up of components that are designed to be positioned in a bifurcated manner with respect to each other, preferably during deployment or repair and support of vessel locations at or near branching sites. Preferably, the graft component is compliant, stretchable or elastomeric and does not substantially inhibit expansion of the tubular support component while simultaneously exhibiting porosity which facilitates normal cellular growth or invasion thereinto of tissue from the body passageway after implantation.

Elastomeric vascular grafts are known to be made by various methods. Included are methods which incorporate electrostatic spinning technology such as that described by Annis et al. in "An Elastomeric Vascular Prosthesis", *Trans. Am. Soc. Artif. Intern. Organs*, Vol. XXIV, pages 209–214 (1978) and in U.S. Pat. No. 4,323,525. Other approaches include elution of particulate material from tubular sheeting, such as by incorporating salts, sugars, proteins, water-soluble hydrogels, such as polyvinyl pyrrolidone, polyvinyl alcohol, and the like, within polymers and then eluting the particulate materials by immersion in water or other solvent, thereby forming pores within the polymer. Exemplary in this regard is U.S. Pat. No. 4,459,252, incorporated by reference hereinto. Another approach involves the forming of pores in polymers by phase inversion techniques wherein a solventized polymer is immersed in another solvent and the polymer coagulates while the polymer solvent is removed. Also known are spinning techniques such as those described in U.S. Pat. No. 4,475,972. By that approach, a polymer such as a polyurethane in solution is extruded as fibers from a spinnerette onto a rotating mandrel. The spinnerette system reciprocates along a path which is generally parallel to the longitudinal axis of the mandrel and at a controlled pitch angle. The result is a non-woven structure where each fiber layer is bound to the underlying fiber layer.

Also known are stent devices, which are placed or implanted within a blood vessel or other body cavity or vessel for treating occlusions, stenoses, aneurysms, disease, damage or the like within the vessel. These stents are implanted within the vascular system or other system or body vessel to reinforce collapsing, partially occluded, weakened, diseased, damaged or abnormally dilated sections of the vessel. At times, stents are used to treat disease at or near a branch, bifurcation and/or anastomosis. This runs the risk of compromising the degree of patency of the primary vessel and/or its branches or bifurcation, which may occur as a result of several problems such as displacing diseased tissue, vessel spasm, dissection with or without intimal flaps, thrombosis and embolism.

One common procedure for implanting a stent is to first open the region of the vessel with a balloon catheter and then place the stent in a position that bridges the diseased portion of the vessel. Various constructions and designs of stents are known. U.S. Pat. No. 4,140,126 describes a technique for positioning an elongated cylindrical stent at a region of an aneurysm to avoid catastrophic failure of the blood vessel wall, the stent being a cylinder that expands to an implanted configuration after insertion with the aid of a catheter. Other such devices are illustrated in U.S. Pat. No. 4,787,899 and U.S. Pat. No. 5,104,399. U.S. Pat. No. 4,503,569 and U.S. Pat. No. 4,512,338 show spring stents which expand to an implanted configuration with a change in temperature. It is implanted in a coiled configuration and then heated in place to cause the material of the spring to expand. Spring-into-place stents are shown in U.S. Pat. No. 4,580,568. U.S. Pat. No. 4,733,665 shows a number of stent configurations for implantation with the aid of a balloon catheter. U.S. Pat. No. 5,019,090 shows a generally cylindrical stent formed from a wire that is bent into a series of tight turns and then spirally wound about a cylindrical mandrel to form the stent. When radially outwardly directed forces are applied to the stent, such as by the balloon of an angioplasty catheter, the sharp bends open up and the stent diameter enlarges. U.S. Pat. No. 4,994,071 describes a bifurcating stent having a plurality of wire loops that are interconnected by an elongated wire backbone and/or by wire connections and half hitches.

Stents themselves often do not encourage normal cellular invasion and can lead to undisciplined development of cells in the stent mesh, with rapid development of cellular hyperplasia. Grafts alone do not provide adequate support in certain instances. Copending application of Jean-Pierre Dereume, Ser. No. 112,774, entitled "Luminal Graft Endoprostheses and Manufacture Thereof" describes grafts that have the ability to carry out dilatation and/or support functions. An expandable tubular support component and an elastomeric graft component are combined into a single device wherein the graft material is secured to either or both of the internal and external surfaces of the expandable support component. The graft material is produced by a spinning technique such as that described in U.S. Pat. No. 4,475,972. Also, luminal endoprostheses with an expandable coating on the surface of external walls of radially expandable tubular supports are proposed in U.S. Pat. No. 4,739,762 and U.S. Pat. No. 4,776,337. In these two patents, the coating is made from thin elastic polyurethane, Teflon film or a film of an inert biocompatible material. A. Balko et al., "Transfemoral Placement of Intraluminal Polyurethane Prosthesis for Abdominal Aortic Aneurysm", *Journal of Surgical Research*, 40, 305–309, 1986, and U.S. Pat. No. 5,019,090 and U.S. Pat. No. 5,092,877 mention the possibility to coat stent materials with porous or textured surfaces for cellular ingrowth or with non-thrombogenic agents and/or drugs. The various patents and publications referred to hereinabove are incorporated hereinto by reference.

By the present invention, grafts which are expandable and supportive are provided that expand from a first diameter to a second diameter which is greater than the first. When it is at its first diameter, the expandable supportive graft is of a size and shape suitable for insertion into the desired body passageway. The material of the graft is substantially inert and preferably has a generally cylindrical cover and/or lining generally over the outside and/or inside surface of the expandable supportive component. Preferably, the cover and/or lining is especially advantageous because it is compliant or elastomeric and porous to encourage desirable growth of tissue thereinto in order to assist in non-rejecting securement into place and avoidance of stenosis development. The porous liner and/or cover material is compliant or elastomeric enough to allow for expansion by up to about 2 to 4 times or more of its unexpanded diameter. Components of the branched or bifurcated expandable supportive endoluminal graft preferably are deployable separately such that each component is properly positioned with respect to the other into the desired branched or bifurcated arrangement. One of the components has a portion which has at least one longitudinally disposed indent to generally define at least two leg portions for receiving one of the other components.

It is a general object of the present invention to provide an improved branched endoluminal graft that is expandable in place and, once expanded, is self-supporting.

Another object of this invention is to provide biocompatible grafts having a plurality of components that are separately expandable in vivo and that are supportive once so expanded.

Another object of the present invention is to provide an improved expandable reinforced graft that is delivered by way of introducers, balloon catheters or similar devices, and which facilitates good tissue ingrowth.

Another object of this invention is to provide an improved endoluminal graft which fully covers diseased or damaged areas for carrying out luminal repairs or treatments, such as repair of aneurysms.

Another object of the present invention is to provide an improved endoluminal graft wherein the endoprosthesis is substantially enclosed within biocompatible compliant material which is presented to the surrounding tissue and blood or other body fluid.

Another object of this invention is to provide an expandable, supportive graft that can be tailored to meet a variety of needs, including a single graft designed to address more than a single objective.

Another object of the present invention is to provide a self-expanding reinforced graft device that is delivered in its elongated and compressed state from within a tubular member and deployed by moving same out of the tubular member, which device is especially suitable for component deployment.

Another object of this invention is to provide a bifurcated trunk component that is deployed in a collapsed state and expanded in vivo to a branched device for use in treatment and/or repair at branched vessel locations.

A further object of the present invention is to provide a component branched endoluminal graft having a longitudinally creased trunk component and at least one cylindrical branch component, which components are expanded separately after endoluminal delivery and which form a bifurcated graft once positioned with respect to each other and expanded.

Another object of this invention is to provide an improved method of forming a branched endoluminal graft incorporating a longitudinal creasing procedure.

Another object of the present invention is to provide an improved method of assembling a branched endoluminal graft.

These and other objects, features and advantages of this invention will be clearly understood through a consideration of the following detailed description.

BRIEF DESCRIPTION OF THE DRAWINGS

The invention will be further elucidated in the following description with reference to the drawings, in which.

DESCRIPTION OF THE PARTICULAR EMBODIMENTS

Figures 1, 2:
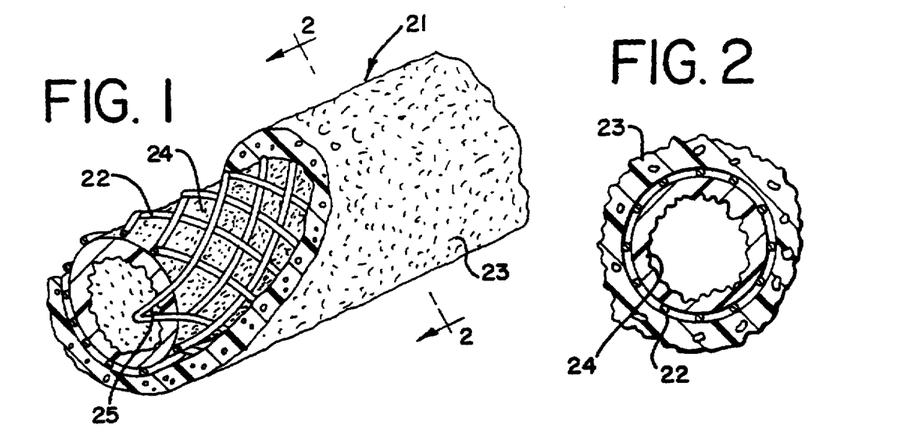
FIG. 1 is a perspective view, partially cut away, of an expandable supportive endoluminal graft construction in accordance with the invention.
FIG. 2 is a cross-sectional view along the line 2—2 of FIG. 1.

An embodiment of expandable supportive luminal graft construction is generally illustrated in FIG. 1 at 21. This embodiment includes a braided tubular support component having generally helically wound rigid but flexible strand or wire elements, some of which have the same direction of winding but are axially displaced from one another, and others of which cross these windings and are also axially displaced with respect to each other. The actual structure can be generally braided as illustrated in Wallsten U.S. Pat. No. 4,655,771, incorporated by reference hereinto, or as found in self-expanding braided flat wire Wallstent® devices. Both a cover 23 and a liner 24 are illustrated in FIGS. 1 and 2. Either cover 23 or liner 24 can be omitted if there is no desire to substantially encapsulate the tubular support component 22.

With more particular reference to the illustrated cover 23 and liner 24, when included, they may be formed by an electrostatic spinning process in this illustrative embodiment. Details regarding electrostatic spinning techniques in general are found in Bornat U.S. Pat. No. 4,323,525 and in Bornat European patent publication No. 9,941, as well as in the Annis et al. article discussed hereinabove, the disclosures of which are incorporated by reference hereinto. With further reference to the application of this technology to the expandable supportable luminal grafts of the present invention, random pattern filaments are formed and electrostatically directed toward a charged mandrel in order to form a random pattern of electrostatically generally cross-linked filaments which take on the configuration of a mat having a cylindrical shape. The filament diameters are particularly fine, as is the pore size of the mat so constructed. A typical range of filament diameters is between about 0.5 micron and about 5 microns, and a typical pore size of the electrostatically spun fiber is between about 3 microns and about 20 microns.

Figure 18:
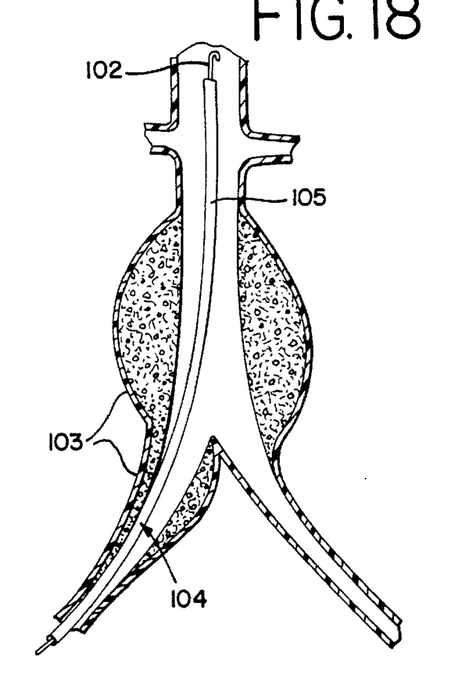
FIGS. 18, 19, 20 and 21 illustrate a component branched graft and various stages of its separate, component deployment within a body vessel to repair an aneurysm, FIGS. 18 and 19 showing deployment of a preferred branched, longitudinally indented trunk component, and FIGS. 20 and 21 showing separate deployment of two branch components within the trunk component.
Figure 19:
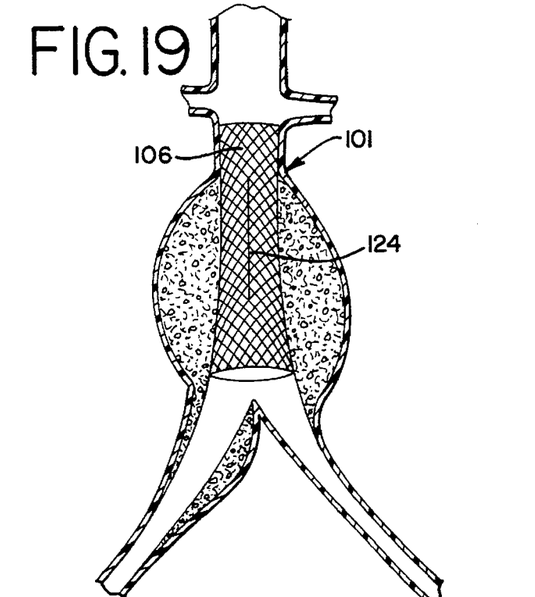
Figure 20:
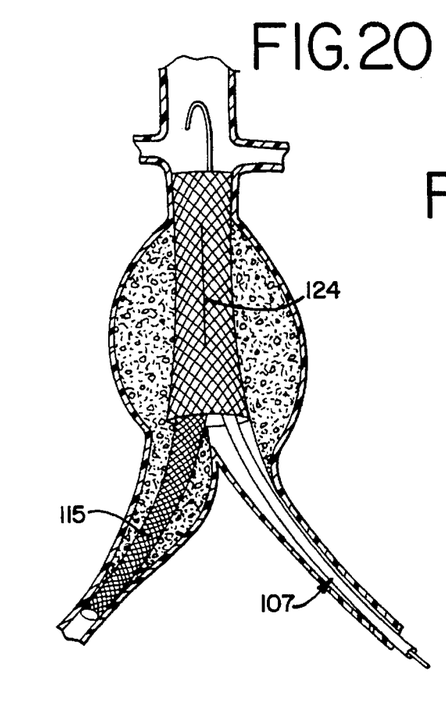

Liner 24 is formed directly on the rotating mandrel by this electrostatic spinning procedure. Thereafter, one of the tubular support components discussed herein, such as the generally braided tubular support 22, is placed over the liner 24 still on the mandrel. In the case of the tubular support 22 in a form that is not spring loaded, this includes longitudinally extending the tubular support 22, such as by pulling one or both of its ends, which thereby decreases its diameter so that it fits snugly over the liner 24. When the generally braided tubular support 22 is of a spring-into-place type, a hold-down member (such as shown in FIGS. 18 and 20) is used to prevent automatic radial expansion prior to deployment. When the expandable supportive graft 21 is to include a cover 23, the mandrel is again rotated, and the electrostatic spinning is again accomplished in order to form the cover 23 directly over the tubular support 22. This will also create some bonding between the thus formed cover 23 and the liner 24 at openings between the strands or wires of the woven tubular support 22 or the like. This bonding can be facilitated by uniformly compressing the outer fibers with a soft silicone roller or sponge such that the still tacky outer fibers bond to the inner fibers thereby encapsulating the tubular support within the graft.

Bonding may also be achieved in this or other embodiments by heat welding and/or by the use of adhesives such as hot melt adhesives, primers, coupling agents, silicone adhesives, and the like, and combinations of these. Examples include aliphatic polycarbonate urethane hot melts and silicone rubber adhesives.

It is important to note that each of the cover 23 and the liner 24, when either or both are present, is made of an elastomeric material which retains its compliant properties after construction of the expandable supportive graft 21 is completed. In this regard, the graft itself is also elastomeric and compliant. Accordingly, the graft 21 is delivered transluminally, such as by being pulled down onto the balloon of a catheter or into an inserter tube and then percutaneously inserted and positioned to the location where the repair is needed. For a non-spring loaded graft, the balloon is then inflated to longitudinally shorten and radially expand the graft 21 into engagement with the vessel walls. Because of the compliance of the cover 23 and/or liner 24, and because of the hoop strength of the braided tubular support 22, the graft 21 will remain in place. In the illustrated embodiment, ends 25 of the tubular support are exposed and are not covered by the cover 23. This allows the exposed end portions 25 to directly engage the vessel wall, if desired in the particular application, in order to assist in anchoring the graft 21 in place. Liner 24 also can be sized so as to not cover the exposed ends 25, or it can extend to or beyond the edge of the ends 25 when it is desired to avoid or minimize contact between the tubular support and the blood or other fluid flowing through the vessel being repaired or treated.

Alternatively, when a braided tubular support such as that illustrated in FIGS. 1 and 2 is incorporated into the graft according to the present invention in a non-spring-loaded form, transluminal delivery can be made by way of a catheter or tool having means for longitudinally compressing the endoprosthesis until it has expanded radially to the desired implanted diameter. Such equipment typically includes a member that engages one end of the endoprosthesis and another member which engages the other end of the endoprosthesis. Manipulation of proximally located controls then effects relative movement of the members toward each other in order to thereby longitudinally compress the endoprosthesis. Delivery tools for spring-loaded grafts include a sleeve that maintains the graft at its compressed diameter until the graft is positioned for deployment such as from the end of an insertion catheter to its auto-expanded state.

Figure 3:
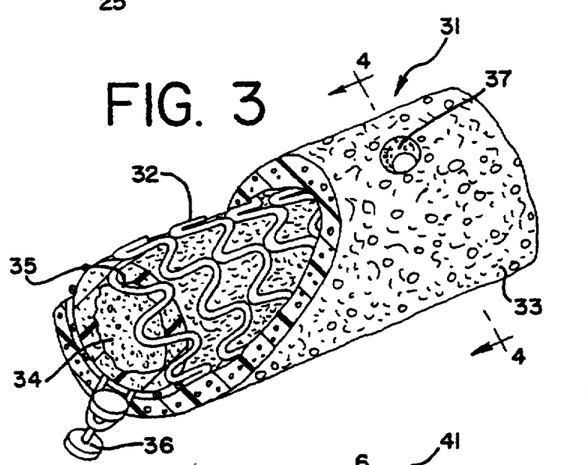
FIG. 3 is a perspective view, partially cut away, of another embodiment of the expandable supportive endoluminal graft construction.
Figure 4:
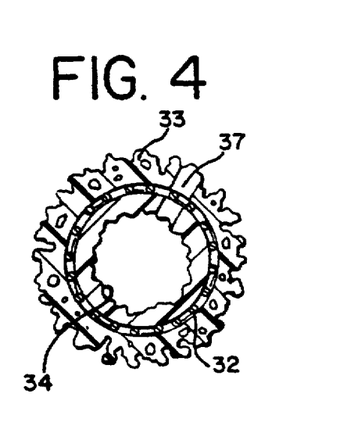
FIG. 4 is a cross-sectional view along the line 4—4 of FIG. 3.

With reference to the embodiment illustrated in FIGS. 3 and 4, an expandable supportive graft is illustrated at 31. The illustrated tubular support component 32 is constructed of sinusoidally configured wire helically wound into a tubular shape. General structures of these types are generally discussed in Pinchuk U.S. Pat. No. 5,019,090, incorporated by reference hereinto. A cover 33 can be positioned over the tubular support 32 and/or a liner 34 can be positioned along its lumen. In this illustrated embodiment, the cover 33 and liner 34 are constructed of porous polymers, the pores thereof having been made by elution or extraction of salts and the like, such as described in MacGregor U.S. Pat. No. 4,459,252, incorporated by reference hereinto. Generally speaking, the porosity is determined by the size of the elutable particles as discussed herein and by the concentration of those particles as a percent by volume of a pre-elution mixture thereof with the polymer of the cover or liner. When a graft 31 having both a cover 33 and a liner 34 is prepared, a mandrel or rod is dipped into a liquid polymer having elutable particles as discussed herein dispersed therewithin. After dipping, the polymer covered rod is contacted with, such as by dipping or spraying, a solvent, for the elutable particles, such as water, thereby forming the eluted porous liner 34. Thereafter, the tubular support 32 is positioned thereover and pressed down into the liner. Then, the rod and the assembly thereon are again dipped into the mixture of polymer and elutable particles, followed by setting and contact with solvent to remove the elutable particles in order to form the eluted porous cover 33. It is also possible to directly extrude the particle-containing polymer into a tubular shape.

Elutable particles which can be used in the making of the eluted porous cover 33 and liner 34 include salts such as sodium chloride crystals, sodium carbonate, calcium fluoride, magnesium sulfate and other water-soluble materials that are readily dissolved by the utilization of water as an elution medium. Other particles that are soluble in organic solvents and the like can be substituted as desired. Further particles include sugars, proteins, and water-soluble hydrogels such as polyvinyl pyrrolidone and polyvinyl alcohol. Suitable polymer materials are as discussed elsewhere herein, the pore size being on the order of about 10 microns to about 80 microns.

As with the other embodiments, when desired, ends 35 of the support component 32 can be exposed either on one or both of its cylindrical faces in accordance with the needs of the particular repair or treatment to be carried out. With this approach, the exposed ends 35 will assist in maintaining the graft 32 in place by mechanical engagement between the exposed ends 35 and the vessel being repaired or treated and/or by tissue ingrowth. The anchoring aspect of the exposed ends of the tubular support can be enhanced by continued radial expansion of the balloon or other deployment means which will permit the exposed ends to expand radially outwardly in an amount somewhat greater than that of the rest of the expandable supportive graft and into the surrounding tissue. It is also contemplated that mechanical means can be used to assist in joining the exposed ends of this embodiment or of other embodiments to the vessel wall. An illustrative example in this regard is the use of transluminally delivered staples which can take on the appearance of rivets. Especially advantageous are staples made of an elastomeric material. Illustrated staples are shown at 36 in FIG. 3. They can be incorporated at other locations as well along the graft. One or more windows 37 can be formed through the cover and/or liner and/or tubular support in order to feed outside branch arteries or other vessels.

Figure 5:
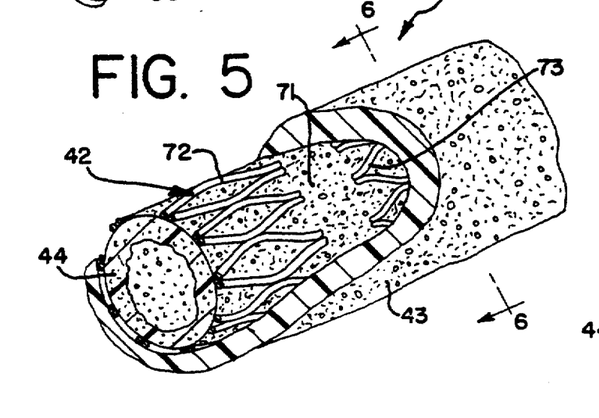
FIG. 5 is a perspective view, partially cut away, of a further embodiment of the expandable luminal graft construction.
Figure 6:
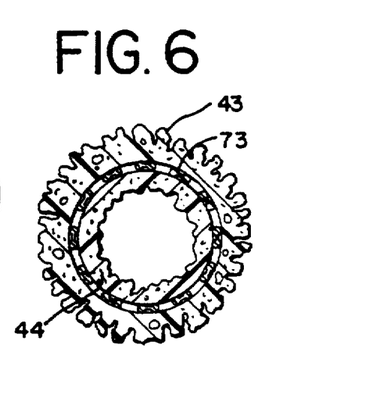
FIG. 6 is a cross-sectional view along the line 6—6 of FIG. 5.

FIGS. 5 and 6 illustrate a further embodiment of an expandable supported graft, generally designated as 41. Shown is a mesh tubular support component, generally designated as 42, such as those of the type illustrated in Palmaz U.S. Pat. No. 4,733,665, incorporated by reference hereinto. These are non-woven mesh-type cylinders or slotted tubes wherein most or all of the individual components are either integrally joined together such as by welding or are integrally formed from a single tube. The resulting endoprostheses are malleable enough so as to be expandable by a balloon of a catheter. Usually, these endoprostheses have particularly high hoop strengths.

Cover 43 and/or liner 44 are made of polymers rendered porous by phase inversion techniques. In accordance with these techniques, a polymer such as a polyurethane is dissolved in a solvent therefor, for example a water-soluble polar solvent, such as dimethyl acetamide, tetrahydrofuran and the like, in order to form what is known as a lacquer. A mandrel or rod is dipped into the lacquer. Thereafter, the dipped rod is contacted with an inversion solvent, such as by dipping in water or a mixture of alcohol and water. This inversion solvent must readily dissolve the polymer solvent of the lacquer, while at the same time being a poor solvent for the polymer. Under these conditions, the polymer coagulates and the polymer solvent of the lacquer is removed and replaced with the inversion solvent. The inversion solvent pulls the polymer solvent out of the polymer on the rod and forms particularly fine pores having a pore size on the order of about 0.5 micron to about 20 microns. The thus formed liner 44 having phase inversion pores is then dried.

Next, the tubular support component 42 is secured over the liner 44 and is preferably radially compressed onto and into the liner. Thereafter, the cover 43 having phase inversion pores is formed in accordance with the same phase inversion steps as discussed hereinabove for preparation of the liner 44. If desired, either the liner or the cover can be omitted. Cover 43 and liner 44 are thus formed in accordance with a displacing step wherein precipitating non-solvent molecules are substituted for non-precipitating solvent molecules dispersed throughout the lacquer coating. This procedure develops advantageous elastic characteristics. Further details regarding the phase inversion procedure are found in Lymann et al. U.S. Pat. No. 4,173,689, incorporated by reference hereinto.

Figures 7, 8, 9, 10:
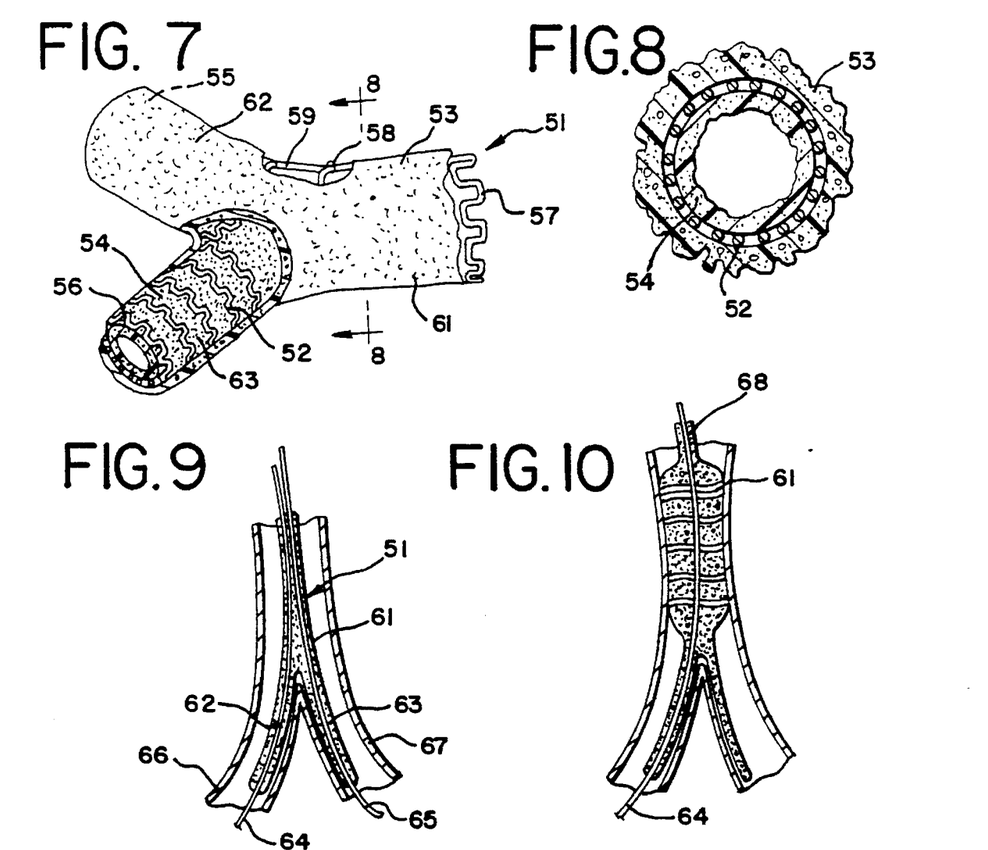
FIG. 7 is a perspective view, partially cut away, of a bifurcated expandable supportive endoluminal graft construction.
FIG. 8 is a cross-sectional view along the line 8—8 of FIG. 7.
FIG. 9 is a somewhat schematic view illustrating an early step in the implantation of a device such as shown in FIG. 7.
FIGS. 10, 11 and 12 are generally schematic views along the lines of FIG. 9 showing expansion of the main body and the branches of this bifurcated device.

FIGS. 7 and 8 illustrate an embodiment wherein the graft takes the form of a bifurcated expandable supportive graft, generally designated at 51. Included is a joined-ring bifurcated tubular support 52. Also shown are a bifurcated cover 53, a bifurcated lining 54 and exposed ends 55, 56, 57. This particular bifurcating graft is well-suited for insertion into a branching vessel.

The tubular support includes a plurality of rings or loops 58 connected by flexible interconnections 59. Constructional details of embodiments of the rings or loops 58 and of the flexible interconnections 59 are found in MacGregor U.S. Pat. No. 4,994,071, incorporated by reference hereinto. The flexible interconnections 59 join the rings or loops 58 into a configuration having a main body or trunk 61 and one or more branches 62. Flexible interconnections 59 extend longitudinally from the axis of each of the main body or trunk 61 and branch 62, 63. At least one such flexible interconnection joins each branch to the trunk. The loops 58 in the main body are substantially parallel to each other, and the loops 58 in each branch 62, 63 are substantially parallel to each other.

The bifurcated cover 53 and bifurcated liner 54 must each, when provided, be especially elastomeric so as to follow the expansion and contraction of the rings or loops 58 that takes place during preparation, transluminal insertion, deployment and the like. Cover 53 and liner 54 will also take on a bifurcated construction. In one embodiment, the liner and/or cover for each of the trunk 61 and branch 62, 63 are made on a cylindrical mandrel, assembled and joined, such as by suitable biocompatible adhesive, fusion, sewing, suturing or other means of joining and/or sealing. Alternatively, a Y-shaped or branched mandrel can be used. The bifurcating liner is then formed thereon by processes such as those discussed herein, including electrostatic spinning, or dipping followed by elution or phase inversion procedures much in the same manner as described herein when straight cylindrical mandrels or rods are used for constructing the non-bifurcated grafts in accordance with this invention. Fiber winding can also be practiced. Bifurcated cover 53 is made in a similar manner by application of the porous cover material over the bifurcated endoprosthesis.

With reference to the bifurcated endoprosthesis, the bifurcated cover 53 and/or bifurcated liner 54 could be made by fiber winding approaches, such as those described in Wong U.S. Pat. No. 4,475,972, the subject matter thereof being incorporated by reference hereinto. Polymer in solution is extruded into fibers from a spinnerette onto a rotating mandrel. The spinnerette is reciprocated along the longitudinal axis of the mandrel at a controlled pitch angle, resulting in a non-woven cylinder wherein each fiber layer is bound to the underlying layer. Control of the pitch angle allows for control of the compliance and kink resistance of the cover and/or liner. In an especially advantageous arrangement when using these fiber spinning techniques in forming an expandable supportive graft in accordance with the general aspects of this invention which has both a liner and a cover, the cover is physically bonded to the liner by the use of an electrostatic field to enable penetration of the cover overlay of fibers through the interstices of the support components in order to improve the bonding of the cover and/or liner fibers to each other and/or to surfaces of the support component.

With more particular reference to balloon deployment of expandable supportive grafts, this is illustrated with some particularity in connection with bifurcated endoluminal grafts in FIGS. 9, 10, 11, 12 and 13. As shown in FIG. 9, two guidewires 64, 65 are inserted into the bifurcating vessel, each of them into different legs 66, 67 of the bifurcating vessel. Thereafter, the unexpanded bifurcated expandable supportive graft 51 is slipped over the proximal ends of the guidewires and routed to the branches of the blood vessel. The unexpanded bifurcated graft can be introduced from an arteriotomy proximal to the bifurcation such as from the brachial artery in the arm, or the unexpanded bifurcated graft can be introduced from the femoral artery in the leg, pushed proximally past the bifurcation and then pulled back distally into both iliacs to form the trunk and bifurcation.

The two branches 62, 63 of the graft 51 are routed separately over the guidewires 64, 65, respectively, and guided, typically with the help of a guide catheter, into the patient until the graft is positioned as shown in FIG. 9. The graft 51 is initially fixed in place as follows. One of the guidewires 65 is removed, and a balloon catheter 68 is inserted into the main body or trunk 61 and inflated to expand the trunk 61 into contact with the vessel walls. This deployment is suitable to secure the graft 51 in place at that location of the vessel.

Figure 11:
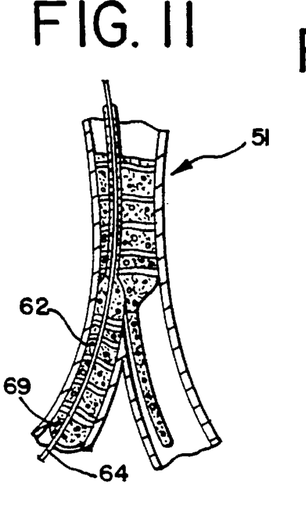
Figure 12:
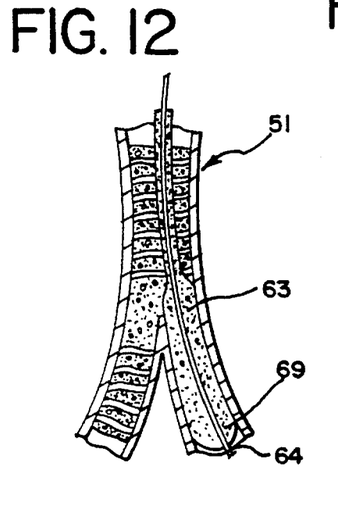
Figure 13:
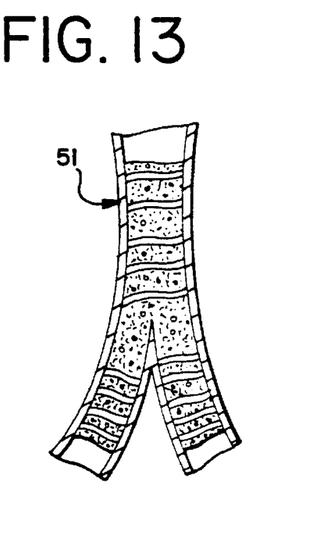
FIG. 13 shows this bifurcated supportive graft after completion of the expansion procedure.

The balloon of balloon catheter 68 is then deflated. If this balloon catheter is also suitable for use in expanding the branches 62, 63 of the graft 51, same is then inserted into an unexpanded branch 62 and radially expanded as generally shown in FIG. 11. If the balloon of catheter 68 is not suitable in this regard, then another balloon catheter 69 effects this function. FIG. 12 shows inflation of the other branch 63 of the graft 51 in a similar manner. FIG. 13 illustrates the fully deployed and expanded bifurcated support graft 51 positioned in place within the bifurcated location. Alternatively, a bifurcated dilation balloon on a bifurcated catheter (not shown) can replace the single-balloon catheter(s) 68, 69.

Preferably the branched and assembled expandable supportive graft is of the spring-into-place type; as such, it will be manipulated to be reduced in diameter and placed within an overlying and bifurcated restraining guiding catheter or the like and will be passed over guidewires and contained within the guiding catheter until proper placement within the bifurcating location. This type of bifurcated expandable supportive graft is deployed by being ejected into place, typically by advancing a small inner catheter through the guiding catheter into contact with the bifurcating graft in accordance with the procedure generally used for spring-into-place stents.

The deployment procedures illustrated in FIGS. 9 through 13 can be characterized as prograde deployment. Retrograde deployment is also possible. The entire bifurcating graft for retrograde deployment is advanced over a single guidewire through one branch of the blood vessel past the point of bifurcation. A second guidewire is then steered down the opposite limb of the graft, and a snare is used. The snare, which is passed retrograde through the opposite vessel, is then used to pull the guidewire into place. Partial balloon inflation in the unbranched or trunk portion of the blood vessel is then used to draw the graft down into position prior to balloon dilatation of both the trunk and branched portions of the graft. Because blood flow is prograde under these circumstances, the contact between the bifurcation of the graft and the bifurcation of the blood vessel helps to prevent the graft from migrating distally, thus reducing the need for active fixation of the graft to the blood vessel.

Figure 14:
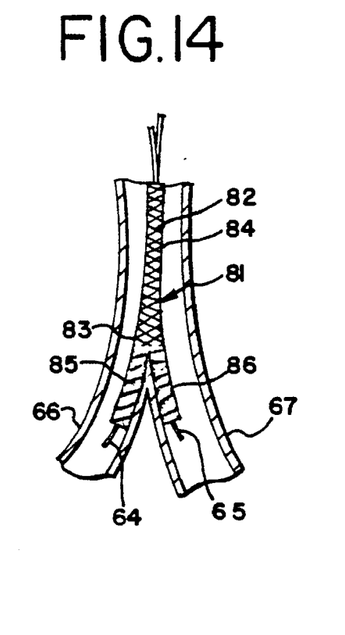
FIG. 14 illustrates another embodiment of a bifurcated expandable supportive endoluminal graft construction.

Another bifurcated endoprosthesis or expandable supportive graft is generally designated 81 in FIG. 14. Separate components are included. In this case tubular supporting component(s) are, prior to deployment, separate from a trunk component. In this embodiment, a fully independent tubular supporting component 82 is located at the trunk position of the graft 81. A bifurcated stretchable wall 83 is in contact with the independent tubular supporting component 82 as either or both of a cover or liner. In addition to being substantially coextensive with the independent tubular supporting component 82 at a trunk portion 84 thereof, the stretchable wall 83 includes at least two generally tubular stretchable branch sleeves 85, 86 which are initially devoid of a supporting component. Separate tubular supporting components 87, 88 (FIGS. 16 and 17) are also included.

Figure 15:
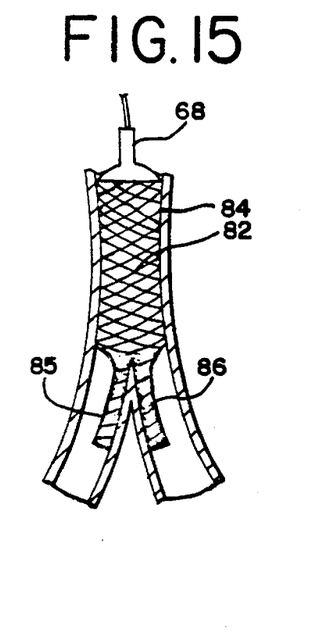
FIGS. 15, 16 and 17 illustrate implantation and assembly of the graft of FIG. 14.

Implantation of this bifurcated expandable supportive graft is depicted in FIGS. 14, 15, 16 and 17. Dual guidewires 64, 65 can be used to properly position the unexpanded bifurcated graft 81 within the bifurcating vessel as shown in FIG. 14. A balloon catheter 68 or similarly functioning device is inserted into the main body of the device so as to expand the independent tubular supporting component 82 and the trunk portion 84 of the bifurcated stretchable wall 83. This deployment initially secures the bifurcated supporting graft into place at that location of the vessel, as shown in FIG. 15. The balloon catheter is then deflated and removed or positioned for use in the next step.

Figure 16:
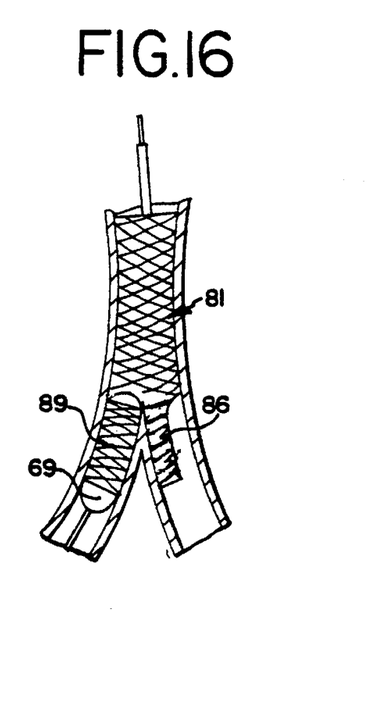
Figure 17:
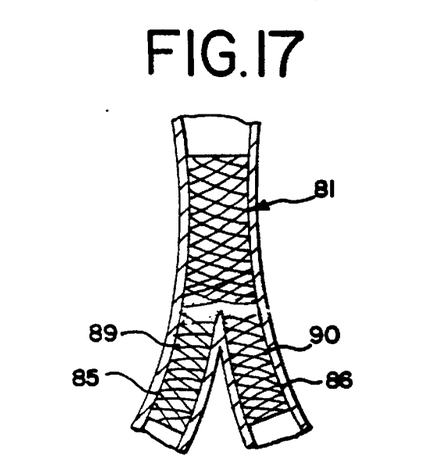

A suitable balloon catheter 69 or the like is next used to deploy and expand in place a branch tubular expandable supporting component 89, as illustrated in FIG. 16. A similar step deploys and expands in place another branch tubular expandable supporting component 90, as generally shown in FIG. 17. The bifurcated stretchable wall 83 and the expandable supporting components may be made with the materials and constructions discussed herein and may be subjected to various treatments as discussed.

A further bifurcated endoprosthesis or expandable supportive graft is one in which the separate components are each expandable supportive graft members. These separate components are illustrated in FIG. 18 through FIG. 21, which also illustrate their separate deployment with respect to each other within an aortic trunk. Same is shown in connection with treating an aneurysm such as an abdominal aorto-iliac aneurysm. The device includes a trunk component 101 which, in the illustrated use, is designed to extend from below the renal arteries to a location between the proximal neck of the aneurysm and the aorto-iliac bifurcation. It will be understood that this trunk component could also be shorter so that it terminates just below the proximal neck of the aneurysm, for example of a length which terminates within the dent or crease 124. In addition, the component bifurcated expandable supportive graft of this embodiment is self-expanding and is deployed by means an introducer containing compressed expandable supportive graft components.

More particularly, and with reference firstly to FIG. 18, a guidewire 102 is first inserted in accordance with known procedures so as to traverse the aneurysm 103. Next, an introducer, generally designed as 104 having the trunk component therewithin in a radially compressed state is inserted over the guidewire 102. The introducer is maneuvered such that it is properly positioned as desired, in this case at a location distal of the distal end of the aneurysm. Then, the sheath 105 of the introducer is withdrawn, such as by sliding it in a proximal direction while the remainder of the introducer 104 remains in place. As the sheath is withdrawn, the trunk 101 expands, eventually achieving the deployed or implanted position shown in FIG. 19. At this stage, the distal portion 106 of the trunk is well anchored into the blood vessel wall and is suitably deployed.

Figure 21:
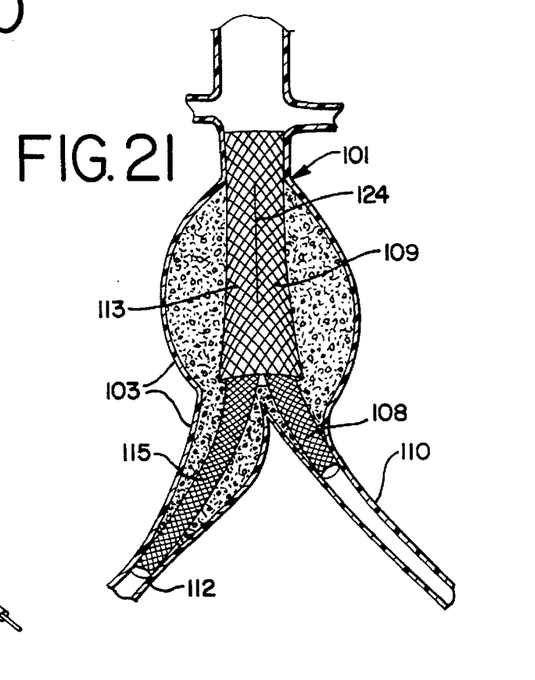

FIG. 20 shows an introducer, generally designated as 107, having an independent tubular expandable supportive graft leg component 108 (FIG. 21) radially compressed therewithin. In this illustrated embodiment, this leg component is an iliac component of the bifurcated supportive graft being assembled within the body vessel. The introducer 107 is advanced until this iliac component is moved into a leg 109 of the already deployed trunk component 101. This positioning is illustrated in FIG. 21. It will be noted that the iliac tubular supportive graft component 108 extends from well within the leg 109 to a location proximal of the aneurysm in the iliac artery 110.

Figures 23, 25, 26, 27, 28, 29, 30:
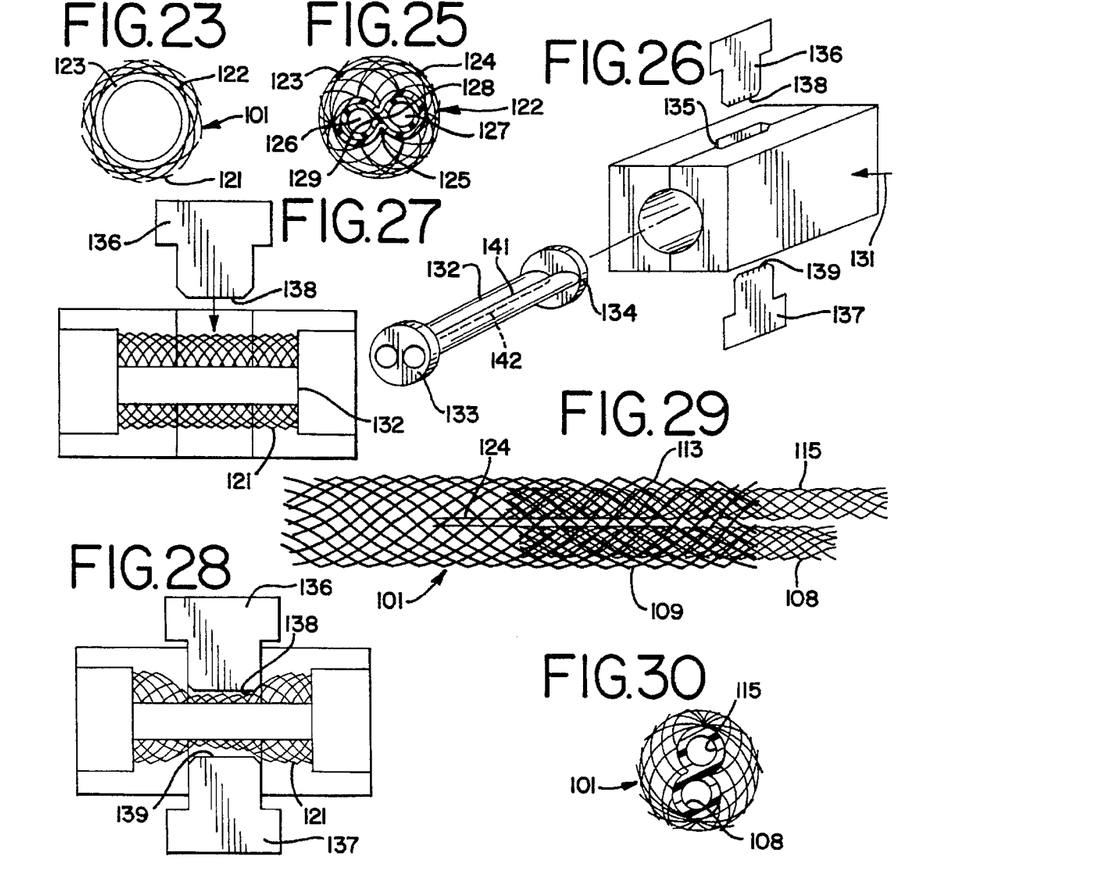
FIG. 23 is a cross-sectional view along the line 23—23 of FIG. 22.
FIG. 25 is an end view of the structure as shown in FIG. 24.
FIG. 26 is a perspective, generally exploded view of an example of a fixture suitable for forming the longitudinal crease in the trunk component according to the present invention.
FIG. 27 is a longitudinal broken-away view of the fixture of FIG. 26 with a braided cylindrical tube positioned therein.
FIG. 28 is a view generally in accordance with FIG. 27, showing formation of opposing crease indents in the braided cylindrical tube during formation of the preferred trunk component.
FIG. 29 is a top plan view showing assembly of supportive endoprosthesis leg components into a branching trunk component according to the invention.
FIG. 30 is an end view of the structure as shown in FIG. 29.
Figure 24:
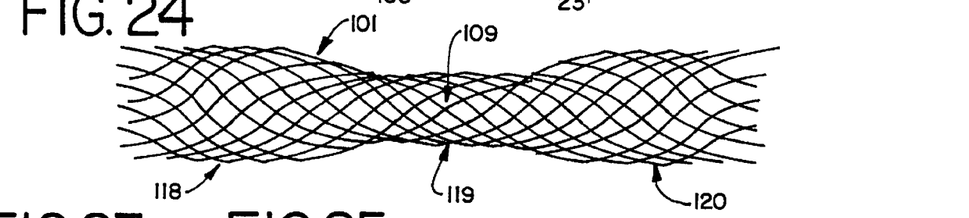
FIG. 24 is a side elevational view of the branching trunk component as illustrated in of FIGS. 22 and 23.

In a previous step, a guidewire had been passed through the appropriate vessel to iliac artery 112 until it crossed the aneurysm 103, while passing through the other leg 113 of the deployed trunk component 101. When the introducer for the previously radially compressed iliac component 115 had been removed, the component 115 had expanded radially and was deployed. Thus, the entirety of the bifurcated endoprosthesis or expandable supportive graft in accordance with this embodiment is fully deployed and assembled together as shown in FIG. 21, as well as generally depicted in FIGS. 29 and 30.

It will be noted that it is not required to actually attach the trunk component 101 and the tubular components 108, 115 together. In other words, these components are generally telescopically positioned with respect to each other. This telescopic feature allows some slippage between the trunk component and the tubular leg components, thereby providing a telescopic joint which functions as a slip bearing. It will be appreciated that it is generally desirable to firmly anchor portions of the bifurcated endoprosthesis within healthy vessel wall tissue. This can be achieved by the hoop strength of the supportive graft or by taking measures to enhance hoop strength at its ends, or by providing grasping structures such as hooks, barbs, flared ends and the like. During pulsetile blood flow and possibly during exercise by the person within which the endoprosthesis is implanted, tension and elongation forces are imparted to the endoprosthesis. In structures that do not have a telescopic joint or some other means to relieve the stress developed by this tension, a considerable amount of stress can be placed on the anchoring sites and/or the attachment components, potentially allowing for dislodgement at the anchoring sites or breakage of attachment components.

FIGS. 22, 23, 24 and 25 further illustrate a trunk component 101. It includes a common trunk portion 118 and a branched portion, generally designated as 119. The branched portion includes the legs 109 and 113. In this embodiment, a further common trunk portion 120 is located opposite the other common trunk portion 118 and extending from the branched portion 119. Thus, the overall configuration of the trunk component is that of a double-lumen length located between two single-lumen lengths. The common trunk portion 118 can be positioned, for example, in the aortic artery, the branched portion 119 provides a bifurcation structure to direct blood flow into the two iliac arteries, and the further common trunk portion 120 facilitates deployment of the leg components into the branched portion 119, acting in the nature of a funnel for each guidewire, introducer and contracted leg component.

Trunk component 101 includes a stent or tubular supporting component 121. Also included is a liner, generally designated as 122. A further liner 123 preferably is located interiorly of the liner 122. Liners 122, 123 are secured within the stent component 121 in order to provide proper porosity for an endoprosthesis.

Trunk component 101 includes one or more indents, such as indent 124 and indent 125. A third, a fourth, or further indents can be provided depending upon the degree of branching desired. It will be appreciated that one or more tubular expandable supportive leg graft components will be provided in order to slide into the branched passageways which are thus defined by the indent(s). In the illustrated embodiment, one such leg component 108 slidingly engages an opening 126 of the trunk component leg 109, while a second leg component 115 slidingly and expansively fits within opening 127 of the leg component 115.

The prosthesis as discussed is deployed to replace or repair tubular bodies such as blood vessels, tracheas, ureters and the like, accommodating more than one conduit in order to divert flow to other branches of the tubular body. This allows for repair of a bifurcated area which is difficult to repair using a single-lumen device or a plurality of individual single-lumen devices. It is suitable for repair of damages branched conduits or, conversely, to repair conduits which converge into a single branch.

A preferred use for the bifurcating endoluminal grafts discussed herein is for insertion into a branching blood vessel. Same is typically suitable for use in the coronary vasculature (the right, left common, left anterior descending, and circumflex coronary arteries and their branches) and the peripheral vasculature (branches of the carotid, aorta, femoral, popliteal arteries and the like). These bifurcated devices are also suitable for implantation into other branching vessels such as in the gastrointestinal system, the tracheobronchial tree, the biliary system, and the genitourinary system.

It will be appreciated that the expandable supportive grafts in accordance with the present invention will dilate and/or support blood vessel lesions and other defects or diseased areas, including at or in proximity to sites of vascular bifurcations, branches and/or anastomoses. The expandable supportive graft is an integral structure that incorporates the expandable support component into the wall or walls of the elastomeric graft. Covers and/or linings that make up the grafts interface with body components that facilitate normal cellular invasion without stenosis or recurrent stenosis when the graft is in its expanded, supportive orientation. The graft material is inert and biocompatible. The expandable supportive graft can be expanded from a smaller diameter insertion configuration to a larger diameter implantation configuration by the application of radially outwardly directed forces provided by expanding the endoprosthesis with a balloon catheter, using an ejection tube that allows a spring-into-place structure to be deployed from the end of a catheter into its expanded configuration, or by using a support component made of certain alloys exhibiting thermotransition characteristics by which they expand when heated, for example.

In addition to the support component structures illustrated herein, support structures include others having spring characteristics and those having a coil with circumferentially oriented fingers such as shown in Gianturco U.S. Pat. No. 4,800,882, incorporated by reference hereinto. U.S. Pat. No. 5,061,275, U.S. Pat. No. 5,219,355 and U.S. Pat. No. 5,336,500 relate to expanding or self-expanding endoluminal devices. Typically, these devices center on the use of a metallic structure imparting expansion attributes. U.S. Pat. No. 4,994,071 and U.S. Pat. No. 5,360,443 describe bifurcated devices which use expandable metallic stent structures and textile materials allowing branching of fluid flow. In general, materials of these patents, incorporated by reference hereinto, can be utilized in constructing components of the present invention.

More specifically, the tubular supportive component preferably is a braided tubular stent body made of metal alloy or any other material that is flexible, while being rigid and resilient when thus braided. Spring-type metals are typically preferred, such as stainless steel, titanium, stainless steel alloys, cobalt-chromium alloys, including alloys such as Elgiloy, Phynox and Conichrome. Thermal transition or memory function alloys such as nickel-titanium alloys including Nitinol are also suitable. Malleable metals including tantalum would be especially suitable for a structure that is not self-expanding.

Concerning the materials for the liner(s), they are typically polymeric materials in the form of a membrane or textile-like material, the objective being to reduce the porosity of the stent for proper tissue ingrowth and fluid tightness. Exemplary polymeric materials include polyesters such as polyethylene terephthalate, polyolefins such as polypropylene, or elastomeric materials such as polyurethane or silicone rubber. Combinations of these materials are also possible. In an especially preferred arrangement, the liner 122 which engages the tubular supportive component 121 is made of a double tricot polyester mesh knit, typically a Dacron type of material, while the interior liner is made of a polyurethane such as Corethane® polymer polycarbonate urethane of Corvita Corporation. In an especially preferred arrangement, a thin coating or cover of polymer is provided over the braided wires of the tubular supportive component. A preferred polymer in this regard is a polycarbonate urethane.

In addition, various surface treatments can be applied to render the surfaces of the expandable supported graft more biocompatible. Included are the use of pyrolytic carbon, hydrogels and the like. The surface treatments can also provide for the elution or immobilization of drugs such as heparin, antiplatelet agents, antiplatelet-derived growth factors, antibiotics, steroids, and the like. Additionally, the coating and/or liner can be loaded with drugs such as those discussed herein, as well as lytic agents in order to provide local drug therapy.

Figure 22:
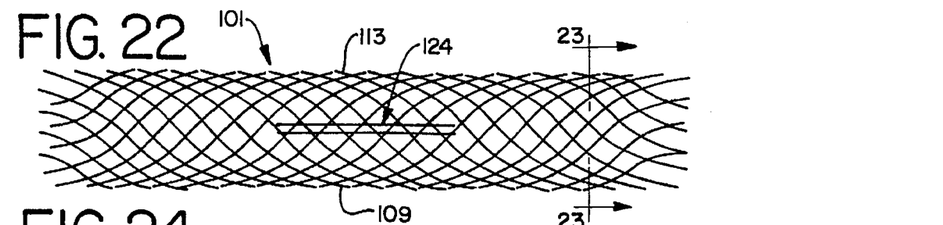
FIG. 22 is a top plan view of a branching trunk component in accordance with the invention.

It will be noted that the indent(s) such as indents 124, 125 are longitudinally disposed and generally define at least two leg portions, each with a diameter less than the diameter of the main body. Each indent has an internal longitudinal surface such as longitudinal edge 128, 129. These edges can be in contact with one another. If desired, they can be secured together such as with sutures, adhesives, wires, clips or the like (not shown). One or two such indents or creases produce an asymmetrical or a symmetrical bifurcation as desired. In another exemplary approach, three indents would form a trifurcated device. Additional creases can be provided insofar as is allowable by the braided wire mesh density and diameter.

Whatever the number of indents, the deformation of the braided tubular body reduces the cross-sectional area from that of the main trunk body to that of each branched area. The total cross-sectional area of the branching tubular bodies should be equal to or greater than 40% of the cross-sectional area of the main trunk body. Preferably, this area should be greater than about 70% in order to prevent any significant pressure differences along the device once deployed and implanted. For example, in a typical human, the cross-sectional area of the abdominal aorta is reduced by only about 20% when opening into the common iliac arteries.

FIG. 26 illustrates a fixture suitable for use in forming the indent or indents as permanent deformations of the braided mesh cylinder which is the tubular supportive component. Fixture 131 in the configuration as illustrated is used for shaping a symmetrical bifurcated design. The braided cylinder is longitudinally compressed and placed over the mandrel 132, this placement being generally shown in FIG. 27. End caps 133, 134 lock the tubular supportive component 121 in its compressed state. Same is then placed into the fixture 131, as generally shown in FIG. 26. Slits 135 are positioned parallel to the longitudinal axis and on opposite sides. This permits the slipping of blades 136, 137 into the fixture 131 and thus into engagement with the tubular supportive component. Edges 138, 139 of the blades then engage and crease the tubular supportive component 121 between the blade edges 138, 139 and the troughs 141, 142 of the mandrel 132.

It will be appreciated that the length of the blade edges 138, 139 can be varied in order to create a desired length of deformation on the main body of the trunk component. In addition, branching areas thus formed can be made of different sizes by varying the size of the individual cylindrical components of the mandrel 132 so they are not identical as shown in FIG. 26. A larger sized mandrel cylinder will result in the formation of a larger trunk component leg 109, 113. This would typically also include shifting the location of the slits 135 so that the plane of blade insertion will line up with the troughs. It will be appreciated that the trifurcated arrangement is achieved by a three-component mandrel and three slits and blades that are 120° apart. Similarly, a four-branched structure would include four of each features, spaced 90° apart.

In a preferred arrangement, the thus deformed braided tubular supportive component is chemically and heat processed in order to set the desired diameter and mechanical properties of the main body. Once this flexible metallic stent with conformed shape is thus prepared, it is preferably lined as discussed elsewhere herein. It will be noted that the illustrated tubular braided mesh has a main cross-sectional area and has an outward flair at both ends. The braided structure is advantageously accommodated by the serrated structure of the blade edges 138, 139 in that the wire elements of the braid are grasped and secured at the ends of the bifurcation.

EXAMPLE I

This example illustrates the formation of a branched expandable supportive endoluminal graft having an expanded internal diameter of 10 mm and which is bifurcated to accommodate two endoluminal supportive graft legs of 5 to 7 mm in diameter. A liner of non-woven polycarbonate urethane (Corethane®) was spun by winding over a mandrel, generally in accordance with U.S. Pat. No. 4,475,972. In this instance, the liner consisted of approximately 400 layers of fibers. A bifurcated braided mesh tubular supportive component made in a fixture as illustrated in FIG. 26 was spray coated using a dilute solution of polycarbonate urethane having a hardness grade and a melting point lower than that used to spin the liner. It was allowed to dry with warm air. Several spray coats allow for the formation of an adhesive layer.

The previously prepared polycarbonate urethane liner was cut to length and placed inside the adhesive-coated bifurcated braided mesh and seated to closely fit the bifurcated braided mesh. A mandrel having a shape similar to the inner configuration of the bifurcated mesh was inserted from one end to act as a support. Shrink tubing was slipped over portions of this assembly. This assembly was heated to the melting point of the polycarbonate urethane adhesive while allowing the shrink tubing to heat shrink and compress the braided mesh against the liner which is supported by the shaped mandrel. After cooling, the shrink tubing was removed and the mandrel slipped out, leaving a completed trunk component as described herein.

The two endoluminal tubular expandable supportive graft leg components are prepared in accordance with a similar procedure which is simpler because of the cylindrical shape of these components.

EXAMPLE II

The procedure of Example I is substantially repeated, except the liner is a double tricot polyester mesh net. In a similar arrangement, a trunk component of the same structure was formed, except prior to insertion of the supporting mandrel, a second, innermost liner of polycarbonate urethane is positioned in order to provide a double-lined branched component.

EXAMPLE III

The procedures of Example I and of Example II are generally followed, except here the expanded inner diameter of the trunk component is 25 mm, and the cylindrical leg endoluminal grafts are 12–15 mm in diameter.

It will be understood that the embodiments of the present invention which have been described are illustrative of some of the applications of the principles of the present invention. Various modifications may be made by those skilled in the art without departing from the true spirit and scope of the invention.

We claim:

1. A multiple-component branching expandable supportive endoluminal graft comprising:

a plurality of expandable supportive endoluminal components which are deployed individually at a selected location within a body vessel, each said supportive endoluminal graft component being radially compressible for endoluminal insertion and radially expandable for deployment at a desired location within a body vessel;

one of said expandable supportive endoluminal components is a trunk component, said trunk component being generally tubular and having a first portion with a given diameter and a second portion including a longitudinally disposed indent generally defining at least two leg portions, each with a diameter less than said given diameter, and each said leg portion has a leg opening;

at least one other of said expandable supportive endoluminal components is a generally cylindrical supportive leg component; and said generally cylindrical supportive leg component and one of said leg portions of the trunk component, when said leg component and trunk component are deployed within the body vessel, are telescopically positioned with respect to each other.

2. The supportive endoluminal graft in accordance with claim 1, wherein said generally cylindrical supportive leg component has an end portion which, when deployed, is positioned within said leg opening of the trunk component.

3. The supportive endoluminal graft in accordance with claim 1, wherein said plurality of expandable supportive endoluminal components are self-expanding.

4. The supportive endoluminal graft in accordance with claim 1, wherein said plurality of expandable supportive endoluminal components are deployed by a radially expandable device.

5. The supportive endoluminal graft in accordance with claim 1, wherein said generally cylindrical supportive component includes a generally cylindrical supporting member and a generally cylindrical liner secured therealong.

6. The supportive endoluminal graft in accordance with claim 1, wherein said trunk component has a trunk liner which includes a compliant wall of essentially inert biocompatible material, said trunk liner being attached to the internal surface of the trunk component, said compliant wall having a diameter size that expands with said trunk component.

7. The supportive endoluminal graft in accordance with claim 5, wherein said liner of the generally cylindrical supportive leg component is a compliant wall of essentially inert biocompatible material, said compliant wall being applied onto at least the internal surface of the generally cylindrical tubular supporting member of the leg component.

8. The supportive endoluminal graft in accordance with claim 1, wherein said trunk component includes a third portion having a diameter approximating said given diameter of the first portion, and said second portion is positioned between said first portion and said third portion.

9. The supportive endoluminal graft in accordance with claim 8, wherein said first portion and said third portion are each generally cylindrical.

10. The supportive endoluminal graft in accordance with claim 1, wherein said generally cylindrical supportive leg component, when deployed, is telescopically slidably positioned within one of said leg portions of the trunk component.

11. The supportive endoluminal graft in accordance with claim 5, wherein said liner of the leg component is a compliant wall made from a porous material that provides a structure which allows normal cellular invasion thereinto from the body vessel when implanted therewithin.

12. The supportive endoluminal graft in accordance with claim 6, wherein said porous material of said compliant wall is an elastomeric polymer.

13. The supportive endoluminal graft in accordance with claim 6, wherein said porous material of said compliant wall is a polycarbonate urethane.

14. The supportive endoluminal graft in accordance with claim 6, wherein said porous material is coated with a thin layer of silicone rubber.

15. The supportive endoluminal graft in accordance with claim 6, wherein said trunk liner includes an interior liner and an intermediate liner between said interior liner and said tubular supporting member.

16. The supportive endoluminal graft in accordance with claim 1, wherein said trunk component includes a plurality of wire strands with open areas therebetween to form a braided mesh.

17. The supportive endoluminal graft in accordance with claim 16, wherein said wire strands of the tubular supporting component include a plurality of individual strands which are longitudinally adjacent to and in contact with each other in a braided, crossing configuration.

18. The supportive endoluminal graft in accordance with claim 1, wherein said generally cylindrical tubular supportive components include wire strands shaped as intersecting elongated lengths integral with each other and defining openings therebetween to form a braided mesh-shaped tubular supporting member.

19. The supportive endoluminal graft in accordance with claim 1, wherein the endoluminal graft is subjected to surface treatment with a compliant adhesive-like polymer.

20. The supportive endoluminal graft in accordance with claim 19, wherein compliant adhesive-like polymer is a polycarbonate urethane.

21. The supportive endoluminal graft in accordance with claim 21, wherein said trunk component has a plurality of said indents, each indent having a longitudinal internal surface, and said longitudinal internal surfaces engage each other to thereby define said leg portion to be generally cylindrical.

22. The supportive branching expandable endoluminal graft in accordance with claim 21, wherein said longitudinal internal surfaces are longitudinal edges that are secured together.

23. A branching expandable supportive endoluminal graft comprising:
an expandable supportive endoluminal graft component which is deployed individually at a selected location within a body vessel, said supportive endoluminal graft component being radially compressible and radially expansible; and
said expandable supportive endoluminal graft component is a trunk component which is generally tubular and has a first portion with a given diameter and a second portion including a longitudinally disposed indent generally defining at least two leg portions, each with a diameter less than said given diameter, and each said leg portion has a leg opening.

24. The branching expandable supportive graft in accordance with claim 23, wherein said trunk component has a plurality of said indents, each indent having a longitudinal internal surface, and said longitudinal internal surfaces engage each other to thereby define said leg portion to be generally cylindrical.

25. The branching expandable supportive graft in accordance with claim 24, wherein said longitudinal internal surfaces are longitudinal edges that are secured together.

26. The branching expandable supportive graft in accordance with claim 23, wherein said trunk component has a polymeric porous wall of essentially inert biocompatible material, said compliant porous wall being applied onto at least said internal surface of the tubular supporting component, and said polymeric wall has a longitudinally disposed crease which lies along said indent of the trunk component.

27. The branching expandable supportive graft in accordance with claim 23, wherein said trunk component includes a third portion having a diameter approximating said given diameter of the first portion, and said second portion is positioned between said first portion and said third portion.

28. The branching expandable supportive graft in accordance with claim 27, wherein said first portion and said third portion are each generally cylindrical.

29. The branching expandable supportive graft in accordance with claim 26, wherein said porous material of said compliant wall is an elastomeric polymer.

30. The branching expandable supportive graft in accordance with claim 26, wherein said porous material of said compliant wall is a polycarbonate urethane.

31. The branching expandable supportive graft in accordance with claim 26, wherein said trunk liner includes in interior liner and an intermediate liner between said interior liner and said tubular supporting member.

32. The branching expandable supportive graft in accordance with claim 23, wherein said trunk component includes a plurality of wire strands with open areas therebetween to form a braided mesh.

33. The branching expandable supportive graft in accordance with claim 23, wherein the endoluminal graft is subjected to surface treatment with a compliant adhesive-like polymer.

34. A method for implanting a multi-component branching expandable supportive endoluminal graft, comprising the steps of:
providing a generally tubular supporting trunk component having a first portion with a given diameter and a second portion including a longitudinally disposed indent generally defining at least two leg portions, each leg portion defining a leg opening having a diameter less than the given diameter of the first portion;
inserting the trunk component generally at a branching site within a body vessel, and expanding the trunk component to engage a main vessel path of the vessel body;
providing a generally cylindrical supportive leg component which includes a tubular supporting member;
inserting the generally cylindrical supportive leg component into the body vessel at a location between a leg portion of the trunk component and a branched pathway associated with a main pathway of the body vessel, and expanding the leg component so as to be deployed at said location;
providing another generally cylindrical supporting leg component having a tubular supporting member; and
inserting the another generally cylindrical supportive leg component into the body vessel at a location between the other leg portion of the trunk component and another branched pathway associated with the main pathway of the body vessel, and expanding the component so as to be deployed at said location in order to form a bifurcated supportive endoluminal graft at a bifurcation site within the body vessel.

35. The method in accordance with claim 34, wherein said step of providing the trunk component includes lining the trunk supporting component, each step of providing the leg component provides a leg component which includes a liner and a tubular supporting member, and each such leg component is deployed inside of a respective one of the leg portions of the trunk component, each of which is generally coextensive with the tubular supporting member of the trunk component.

36. A method for manufacturing a branched expandable supportive endoluminal graft, comprising the steps of:

forming a cylindrical braided mesh tube by braiding metal strands into a cylindrical member;

crimping longitudinal portions of the cylindrical braided mesh tube to form at least one longitudinally disposed indent therein to provide a crimped braided mesh tube;

attaching an adhesive layer to the inside surface of the crimped braided mesh tube;

inserting a cylindrical polymeric compliant tube within the crimped braided mesh tube into engagement with the adhesive layer; and applying pressure to secure the polymeric compliant tube onto the inside surface of the crimped braided mesh tube and simultaneously form a crease in the polymeric compliant tube that generally conforms in shape and size to the indent of the crimped braided mesh tube.

* * * * *

UNITED STATES PATENT AND TRADEMARK OFFICE
CERTIFICATE OF CORRECTION

PATENT NO. : 5,632,772
DATED : May 27, 1997
INVENTOR(S) : Rysler Alcime, Yasushi Kato and Leonard Pinchuk It is certified that error appears in the above-indentified patent and that said Letters Patent is hereby corrected as shown below:

On the Cover Page, under "References Cited", "U.S. PATENT DOCUMENTS", delete line 6 "4,555,771  11/1985  Wallsten" and replace it with --4,655,771  4/1987  Wallsten--; under "FOREIGN PATENT DOCUMENTS", line 1, delete "79302040" and replace it with --79302040.5--; line 2, delete "91304988" and replace it with --91304988.8--.

In the drawings, delete sheet 1 of 5, and replace it with the attached sheet of drawings, FIGS. 1-6.

Col. 3, line 49, "in vivo" should be in italics.
Col. 4, line 51, delete "of" before "FIGS. 22 and 23".
Col. 11, line 3, insert --of-- after "means".
Col. 12, line 39, delete "damages" and insert --damaged--.
Col. 17, line 28, delete "claim 21," and insert --claim 1,--.
Col. 18, line 21, delete "includes in" and insert --includes an--.

Signed and Sealed this

Twenty-eighth Day of October, 1997

Attest:

BRUCE LEHMAN

Attesting Officer

Commissioner of Patents and Trademarks